United States Patent [19]

Cercek et al.

[11] Patent Number: 5,231,002
[45] Date of Patent: Jul. 27, 1993

[54] SYNTHETIC SCM-ACTIVE CANCER RECOGNITION PEPTIDES

[76] Inventors: Boris Cercek; Lea Cercek, both of 4318 Camphor Ave., Yorba Linda, Calif. 92686

[21] Appl. No.: 581,067

[22] Filed: Sep. 6, 1990

Related U.S. Application Data

[63] Continuation of Ser. No. 163,250, Mar. 2, 1988, abandoned.

[51] Int. Cl.$^5$ .................... G01N 33/574; C07K 7/06; C07K 7/08; C07K 7/10
[52] U.S. Cl. .................................. 435/724; 530/329; 530/328; 530/327; 530/326; 530/325; 530/324
[58] Field of Search ............... 435/7.24; 530/329, 328, 530/327, 326, 325, 324

[56] References Cited

U.S. PATENT DOCUMENTS 4,038,282  7/1977  Hirschmann et al. .......... 260/295 D
4,657,892  4/1987  Brantl ............................. 530/329 X

FOREIGN PATENT DOCUMENTS

WO87/07382  12/1987  PCT Int'l Appl. .

OTHER PUBLICATIONS

Whitham et al., Biochem J. 240, 913-916 (1986).
A. A. Gershkovich, V. K. Kibirev, S. B. Serebryanyi, Ya. T. Terletskaya, E. P. Kozulina, & Ya. V. Belik, "A Study of the Properties of Synthetic Analogs of the Tryptophan-Containing Fragment 113-121 of the Basic Protein of Myelin," *Khimiya Prirodnykh Soedinenii* 4, 557-565 (1979) (translated from Russian).
S. Levit, J. M. Powers, D. Milek, & S. W. Brostoff, "Peptide Length Requirement for Experimental Allergic Encephalomyelitis in Guinea Pigs," Neurochem. Res. 5, 37-42 (1980).
Suzuki et al., "Studies on Encephalitogenic Fragments of Myelin Protein . . . ", Chem Pharm. Bull. 22(9), 2181-2187 (1974).
Deber et al., "Association of Carbon-13 Enriched Human Encephalitogenic Nonapeptide . . . ", J. Biol. Chem 254(14), 6341-45 (1979).
L. Cercek, B. Cercek, C. I. V. Franklin, "Biophysical Differentiation Between Lymphocytes from Healthy Donors, Patients with Malignant Diseases and Other Disorders," *Brit. J. Cancer* 29, 345-352 (1974).
(List continued on next page.)

Primary Examiner—Christine M. Nucker
Assistant Examiner—M. P. Woodward
Attorney, Agent, or Firm—Sheldon & Mak

[57] ABSTRACT

The SCM (structuredness of cytoplasmic matrix) test is a means of distinguishing lymphocytes isolated from mammalian donors, including humans, afflicted with cancer from lymphocytes isolated from donors free of malignancy. The test comprises contacting the lymphocytes with a challenging agent and then observing a decrease in the structuredness of the cytoplasmic matrix in lymphocyte from donors with cancer; lymphocytes from donors without cancer show no decrease in structuredness. Preferably the decrease in structuredness is quantified by measuring the fluorescence polarization for an extrinsic fluor added to the cells and observing a decrease in fluorescence polarization after lymphocytes from a donor with cancer have been contacted with a challenging agent. Among the challenging agents useful in the SCM test are several synthetic peptides which are the subject of the present invention. These peptides, of which two have the amino acid sequences Phe-Trp-Gly-Ala-Gly-Gln-Arg (I) and Phe-Trp-Gly-Ala-Glu-Gly-Gln-Arg (II), react with lymphocytes from donors with any type of malignancy. Also among the aspects of the present invention are several other peptides expected to have SCM activity because of their close structural relationship to peptides I and II, methods of using the synthetic SCM-active peptides in tests for the presence or absence of malignancy, antibodies specifically binding the synthetic peptides, including monoclonal antibodies, and genetic probes consisting of DNA sequences corresponding to the amino acid sequences of the synthetic SCM-active peptides.

20 Claims, No Drawings

OTHER PUBLICATIONS

L. Cercek & B. Cercek, "Application of the Phenomenon of Changes in the Structuredness of Cytoplasmic Matrix (SCM) in the Diagnosis of Malignant Disorders: a Review," *Europ. J. Cancer* 13, 903–915 (1977).

L. Cercek & B. Cercek, "Changes in SCM–Responses of Lymphocytes in Mice After Implantation with Ehrlich Ascites Cells," *Europ. J. Cancer* 17, 167–171 (1981).

L. Cercek & B. Cercek, "Changes in the SCM Response Ratio ($RR_{SCM}$) After Surgical Removal of Malignant Tissue," *Brit. J. Cancer* 31, 250–251 (1975).

L. Cercek & B. Cercek, "Apparent Tumour Specificity with the SCM Test," *Brit. J. Cancer* 31, 252–253 (1975).

Spinco Brochure DS–404, "Experimental Allergic Encephalitogenic Peptide (Human)".

R. B. Wallace, M. J. Johnson, T. Hirose, T. Miyake, E. H. Kawashima, & K. Itakura, "The Use of Synthetic Oligonucleotides as Hybridization Probes. II. Hybridization of Oligonucleotides of Mixed Sequence to Rabbit–Globin DNA," *Nucl. Acids Res.*, 9, 879–894 (1981).

R. Lathe, "Snythetic Oligonucleotide Probes Deduced from Amino Acid Sequence Data: Theoretical and Practical Considerations," *J. Mol. Biol.* 183, 1 (1985).

M. Deutsch & A. Weinreb, "Validation of the SCM-Test for the Diagnosis of Cancer," *Eur. J. Cancer Clin. Oncol.* 19, 187–193 (1983).

SYNTHETIC SCM-ACTIVE CANCER RECOGNITION PEPTIDES

This is a continuation of co-pending application Ser. No. 07/163,250 filed on Mar. 2, 1988, now abandoned.

CROSS-REFERENCES

This invention is related to three prior patent applications, all by Dr. Boris Cercek and Dr. Lea Cercek: Ser. No. 838,264, filed Mar. 10, 1986 and entitled "Automated Collection of Buoyant Density Specific Cells from Density Gradients," Ser. No. 022,759, filed Mar. 6, 1987 and entitled "Blood Plasma Factors Related to Cancer," and Ser. No. 867,079, filed May 27, 1986, and entitled "Method for Measuring Polarized Fluorescence Emissions." The disclosure of these three patent applications are incorporated herein by this reference.

FIELD OF THE INVENTION

This invention is directed to cancer detection tests.

BACKGROUND OF THE INVENTION

1. Prior Art

Many diseases occurring in humans and animals can be detected by the presence of foreign substances, particularly in the blood, which are specifically associated with the disease or condition. Tests for antigens or other such substances produced as a result of such diseases show great promise as a diagnostic tool for the early detection and treatment of the particular disease that produced the antigen or other substance. A procedure for the detection of such substances must be reliable, reproducible, and sensitive in order to constitute a practical diagnostic procedure for health care providers. In addition, any such procedure should be able to be carried out by persons of ordinary skill and training in laboratory procedures, and should be relatively fast and inexpensive to carry out.

For example, in the treatment of the various malignancies that afflict humans and animals, referred to generally as cancer, it is recognized that early detection is a key to effective treatment, especially as many therapeutic procedures are effective only in relatively early stages of the disease. In fact, virtually all known cancer treatments are not only more effective, but safer, in early stages of cancer. Far too many cases of cancer are only discovered too late for effective treatment.

Accordingly, there is a great need for reliable tests which can diagnose cancer at early stages. In this connection new tests and procedures are being developed to effect early diagnosis of the cancer.

One extremely desirable aspect of such a test is its ability either to detect all types of cancer generally, or to detect specific types of cancer, depending on the materials used. The former application of such a test is very important in mass screening of large patient populations, as would be done in routine checkups. In such mass screenings a test dependent on a particular type of cancer would not be desirable, as there are literally hundreds of types of cancer and a test that could spot only one or a few types of the disease is far too likely to miss many cases of caner. In general, these patients would present either no symptoms or vague generalized symptoms that could not be readily linked to a particular type of cancer, so there would be no basis for suspecting a particular type and administering a test specific for that type.

In contrast, once the presence of malignancy is known or strongly suspected, it would be desirable to have a test that could pinpoint the particular type of malignancy present. Such a test could add greatly to the efficacy of treatment, because many of the most effective cancer therapies, such as chemotherapy, are only effective against one type of cancer or at best, a narrow range of types, and the wrong chemotherapy can do more harm than good.

We have developed and reported one such test for the early detection of cancer in L. Cercek, B. Cercek, and C. I. V. Franklin, "Biophysical Differentiation Between Lymphocytes from Health Donors, Patients with Malignant Diseases and Other Disorders," *Brit. J. Cancer* 29, 345–352 (1974) and L. Cercek and B. Cercek, "Application of the Phenomenon of Changes in the Structuredness of Cytoplasmic Matrix (SCM) in the Diagnosis of Malignant Disorders: a Review," *Europ. J. Cancer* 13, 903–915 (1977).

Our SCM (structuredness of cytoplasmic matrix) test takes advantage of the fact that a subpopulation of the lymphocytes of a normal individual alters their internal structure in response to challenge by a mitogen such as phytohaemagglutinin (PHA), and does not respond to challenge by certain challenging agents, including certain cancer-associated antigens, while the lymphocytes of an individual with cancer respond in just the reverse way. In other words the same subpopulation of lymphocytes from cancer patients does not respond in the SCM test to challenge by a mitogen, but does respond strongly to challenge by a number of cancer-associated antigens, as well as by the synthetic peptides which are the subject of the present invention.

Depending on the substance used to challenge the lymphocytes (the challenging agent), the SCM test can be made to detect either cancer generally or a specific type of cancer. As will be detailed, the SCM test shows considerable promise in detecting early malignancies, and therefore, has potential clinical usefulness.

The changes seen in the SCM test are believed to reflect changes in the internal structure of the lymphocyte as the lymphocyte is activated for synthesis. These changes are seen as a decrease in the fluorescence polarization of the cells when polarized light is used to excite an extrinsic fluor, fluorescein, generated intracellularly by the hydrolysis of a nonfluorescent compound, fluorescein diacetate, which has been absorbed by the lymphocytes. It is necessary to add an extrinsic fluor since the intrinsic fluorescence of cellular components is too small to give results in this test. Therefore, all references to fluorescence polarization values herein are references to fluorescence polarization values obtained with an extrinsic fluor, preferably one generated intracellularly by enzymatic hydrolysis from a nonfluorogenic compound added to and absorbed by the cells.

When measuring fluorescence polarization in the SCM test, the important value to calculate is the net value of fluorescence polarization, "P", after correction is made for (i) the intrinsic fluorescence of the medium, (ii) any extracellular fluorescein present, and (iii) the unequal transmission of the two components of polarized light in the fluorescence polarization measurement apparatus. All references hereinafter to measurements of the fluorescence polarization are to measurements of the net value of the fluorescence polarization unless otherwise specified. Fluorescence polarization is a measure of intracellular rigidity; the greater the fluidity of intracellular mobility, the less the measured fluorescence polarization. As seen in the SCM test, the observed decrease in fluorescence polarization, as measured by a decrease in the P value, is thought to result mainly from changes in the conformation of the mitochondria, the energy-producing organelles of the cell. The changes in the mitochondria are believed to result from the contractions of the cristae or inner folds of the mitochondrial membrane. The SCM reflects the forces of interaction between macromolecules and small molecules such as water molecules, ions, adenosine triphosphate, and cyclic adenosine phosphate. Perturbations of these interactions results in changes in the SCM.

Not all lymphocytes respond positively in the SCM test; only about 10-20% of lymphocytes actually respond. Immunologically the SCM-responding lymphocytes are T-cell mononuclear leukocytes. These lymphocytes which do respond form a subpopulation which can be isolated by methods such as density gradient centrifugation. This subpopulation is referred to hereinafter as "potentially SCM-responding lymphocytes."

The SCM test is capable of responding to a relatively small quantity of malignant cells. About $10^9$ cells in a person with body weight 70 kg are enough to cause the lymphocytes to respond in the SCM test in the characteristic pattern of malignancy. In mice, when as few as $7.5 \times 10^5$ Ehrlich ascites (tumor) cells are implanted, the pattern of the response in the SCM test is altered; response to cancer-specific antigens is induced, while the normal response to PHA is virtually eliminated. (L. Cercek and B. Cercek, "Changes in SCM-Response of Lymphocytes in Mice After Implantation with Ehrlich Ascites Cells," *Europ. J. Cancer*, 17, 167-171 (1981)).

By contrast, when malignancies of the breast or colon are surgically removed, the response of the surgical patients' lymphocytes to a generally cancer-associated antigen, cancer basic protein (CaBP), is lost within 24 hours after surgery. The normal response to PHA is slower to recover in these patients; that response returns within two weeks after surgery (L. Cercek and B. Cercek, "Changes in the SCM Response Ratio ($RR_{SCM}$) After Surgical Removal of Malignant Tissue," *Brit. J. Cancer* 31, 250-251 (1975)).

For comparison of the response of lymphocytes to cancer-associated antigens and to PHA in the SCM test, an "SCM Response Ratio" can be calculated. This ratio is the ratio of the degree of fluorescence polarization obtained after stimulation with a cancer-associated antigen to the degree of fluorescence polarization obtained after stimulation with PHA. Since normal cells show a decrease in fluorescence polarization after treatment with PHA, but not with cancer-associated antigens, the response ratio for such normal cells is generally relatively high—from 1.3 to 1.6. By contrast, lymphocytes isolated from patients with malignant conditions show a much lower response ratio of 0.6 to 0.8. In some "premalignant" conditions such as polyposis coli and hyperkeratosis of the skin, an intermediate ratio of 0.8 to 1.0 may be seen. (Cercek, Cercek and Franklin, 1974). This suggests that the SCM test may have diagnostic value even before the cancer has reached a clinically or histologically detectable stage.

When lymphocytes from cancer patients are challenged in the SCM test with pieces of whole cancer tissue, they respond only to tissues of the same types of cancer from which the lymphocytes were derived (L. Cercek and B. Cercek, "Apparent Tumour Specificity with the SCM Test," *Brit. J. Cancer* 31, 252-253 (1975)).

However, the purified cancer-associated antigens which are the subject of this invention do not give a response specific for a particular type of cancer when used to challenge lymphocytes in the SCM test. In other words, these purified antigens elicit a response in lymphocytes from patients with any type of cancer. As discussed previously, this property may make such antigens clinically useful for generalized screening tests. However, the response to the SCM test may fail at extremely advanced stages of malignant disease, when the cancer has already metastasized.

Among the cancer-associated antigens which are known to be effective in the SCM test are cancer basic protein (CaBP) and myelin basic protein (MBP). Cancer basic protein is a basic protein or group of similar basic proteins isolated from cancerous tumors. Myelin basic protein (MBP) is an approximately 15,000 dalton protein which is a major component of myelin. An abnormal allergic response to myelin is believed to be part of the disease process in a number of nervous system disorders, such as Guillain-Barre' syndrome and very likely multiple sclerosis. As expected, lymphocytes from multiple sclerosis respond to MBP in the SCM test; however, such lymphocytes do not respond to CaBP, and respond as do lymphocytes from normal individuals to PHA. This pattern of responses differentiates lymphocytes from patients with multiple sclerosis from lymphocytes from patients with malignant disorders.

However, neither CaBP nor MBP is ideal for use as a generalized challenging agent in the SCM test. Both must be purified from natural material, which creates the possibility of variability from batch to batch, as well as the possibility of contaminants having a profound effect on the test. CaBP, furthermore, is a relatively nonspecific antigen, and it has therefore fallen into disfavor. MBP is relatively difficult to purify, as the starting material is central nervous system material, and the protein is relatively hydrophobic and insoluble under many conditions. Furthermore, it is known that lymphocytes from patients with multiple sclerosis respond to MBP in the SCM test. Although the response of such lymphocytes can be differentiated from the response given by lymphocytes from patients with malignancies, such differentiation requires extra controls, such as stimulation of an aliquot of the lymphocytes with a mitogen, and complicates the test.

When synthetic experimental allergic encephalitogenic peptide (EAE peptide) became available, this peptide, which is a fragment comprising amino acid residues 114-112 of human MBP and having the amino acid sequence Phe-Ser-Trp-Gly-Ala-Glu-Gly-Gln-Arg, was tested in the SCM test and gave the expected positive response similar to MBP. This EAE was distributed commercially by Beckman Instruments.

2. Research Leading to the Invention

The research which led directly to the present invention began when the inventors, in work not published or revealed prior to this application, most unexpectedly discovered that Beckman EAE peptide further purified by anion-exchange chromatography did not produce the expected response in the SCM test when used to challenge lymphocytes from cancer patients. Thus the synthetic peptide that was expected to be useful in the SCM test proved to be a failure.

Accordingly, there is a need for a peptide useful as a substitute for cancer basic protein and myelin basic protein as a challenging material for lymphocytes from cancer cells in the SCM test. Preferably the peptide is nonspecific with respect to the type of cancer affecting the donor of the challenged lymphocytes. It is desirable that the peptide be useful for rapid screening of lymphocyte samples for cancer with the SCM test and be useful for detecting cancer in its early stages. A composition comprised of such peptides is designated an "SCM-active cancer recognition composition," or, since the recognition of cancer is the major purpose of the test and any composition must have that activity to be of value in the test, more simply as an "SCM-active composition."

SUMMARY

The represent invention is directed to a class of peptides that satisfies this need. An SCM-active cancer recognition composition according to the present invention comprises substantially only peptides of this class, the peptides having at least seven amino acid residues including a sequence of Phe-Trp-Gly-$R_1$ therein, where $R_1$ is selected from the group consisting of Ala and Val. Preferably, the composition contains only one peptide of this class.

Preferably the peptide has the sequence Phe-Trp-Gly-$R_1$-$R_2$-Gly-$R_3$-Arg therein, where $R_1$ is selected from the group consisting of Ala and Val, $R_2$ is selected from the group consisting of Glu and Asp, and $R_3$ is selected from the group consisting of Asn and Gln. More preferably, the peptide has the amino acid sequence Phe-Trp-Gly-Ala-Glu-Gly-Gln-Arg, and the composition is substantially free of experimental allergic encephalitogenic peptide.

Alternately, preferably the peptide has the amino acid sequence of Phe-Trp-Gly-$R_1$-Gly-$R_3$-Arg therein, where $R_1$ is selected from the group consisting of Ala and Val and $R_3$ is selected from the group consisting of Gln and Asn. More preferably, the peptide has the amino acid sequence Phe-Trp-Gly-Ala-Gly-Gln-Arg, and the composition is substantially free of experimental allergic encephalitogenic peptide.

Another aspect of the present invention is directed to methods of employing the SCM-active compositions in the SCM test. Most generally, this method comprises the testing of lymphocytes from a mammalian donor for the presence or absence of malignancy in the donor by contacting a suspension of the lymphocytes with the SCM-active composition. The method further comprises the step of determining the decrease in the structuredness of the cytoplasmic matrix of the lymphocytes resulting from the step of contacting the suspension with the SCM-active composition. A preferred method for quantifying the decrease in structuredness is to: (1) measure the decrease in fluorescence polarization resulting from the contacting of the lymphocytes, by measuring the fluorescence polarization, $P_s$, for an aliquot of the lymphocytes which has been contacted with the SCM-active composition; (2) measure the fluorescence polarization, $P_c$, for a control aliquot of the lymphocytes which has not been contacted; and (3) determine the ratio of $P_s$ to $P_c$. A ratio of $P_s$ to $P_c$ lower than about 0.9 indicates a positive response to the SCM-active composition and the presence of a malignancy in the donor of the lymphocytes.

A more preferred method comprises comparing $P_s$ to the fluorescence polarization of another aliquot of the lymphocytes contacted with a mitogen, $P_M$, to determine an SCM response ratio, $RR_{SCM}$, where:

$$RR_{SCM} = P_s/P_m.$$

An $RR_{SCM}$ of less than about 0.8 indicates the presence of a malignancy in the donor of the lymphocytes.

An additional aspect of the present invention is directed toward genetic probes comprising DNA sequences corresponding to the known amino acid sequences of the synthetic peptides described herein as having SCM activity. Such genetic probes can be useful in screening DNA of cancer cells for genes homologous to the sequence coding for the synthetic peptides and therefore possibly associated with cancer.

The DNA sequence comprises a sequence corresponding to the amino acid sequence of Phe-Trp-Gly-$R_1$, where $R_1$ is selected from the group consisting of Ala and Val. Preferably, the DNA sequence comprises a sequence corresponding to the amino acid sequence Phe-Trp-Gly-Ala-Glu-Gly-Gln-Arg. Alternatively, the DNA sequence comprises a sequence corresponding to a peptide of the amino acid sequence Phe-Trp-Gly-Ala-Gly-Gln-Arg.

Still an additional aspect of the present invention includes antibodies produced by covalently coupling any of the classes of peptides hereinbefore described as comprising the SCM-active composition, or, alternatively, substantially purified peptides of the amino acid sequence Phe-Trp-Gly-Ala-Gly-Glu-Gln-Arg or Phe-Trp-Gly-Ala-Gly-Gln-Arg substantially free of experimental allergic encephalitogenic peptide to a high molecular weight carrier and immunizing an animal with the resulting covalent conjugate. The antibodies produced are specific for the SCM-active cancer recognition composition. Preferably, the high molecular weight carrier is keyhole limpet hemocyanin, and the covalent coupling is carried out by reaction with a carbodiimide.

Still an additional aspect of the present invention encompasses the production of monoclonal antibodies specific for any of the classes of peptides hereinbefore described as comprising the SCM-active composition or the substantially purified single peptides. This aspect includes cells producing antibodies against any of these classes of peptides or the substantially purified single peptides, immortal cells producing such antibodies and resulting from the fusion of such antibody-producing cells with myeloma cells, and monoclonal antibodies produced by such immortal cells.

Still another aspect of the present invention is directed to a process for detecting lymphocytes capable of binding the peptide of amino acid sequence Phe-Trp-Gly-Ala-Gly-Gln-Arg, or Phe-Trp-Gly-Ala-Gly-Gln-Arg. The process comprises the steps of isolating potentially SCM-responding lymphocytes, incubating the peptide with the isolated lymphocytes to produce a lymphocyte-peptide complex, binding an antibody specific for the SCM-active peptide used in producing the complex to that complex, and detecting the antibody bound. Preferably, the antibody can be a monoclonal antibody. Also, the antibody bound to the lymphocyte-peptide complex can be detected by the presence of a fluorescent or radioactive label on the antibody, or the use of a second enzyme-linked antibody specific for the anti-peptide antibody and the performance of an enzyme-linked immunosorbent assay.

The compositions and peptides of the present invention, when used with the SCM test or with the immunochemical assays hereinafter described, provide sensitive, reproducible, and relatively simple means for detecting malignancies at an early stage.

DESCRIPTION

This invention relates to particular synthetic peptides useful as the challenging agent in the SCM test for cancer detection. The peptides have a length of least seven amino acid residues and include a sequence of Phe-Trp-Gly-$R_1$ therein, where $R_1$ is selected from the group consisting of Ala and Val.

A method for purifying and characterizing these peptides will now be described, as well as methods of using them in the SCM test, of constructing genetic probes of DNA sequences corresponding to the amino acid sequences of the peptides, of producing antibodies, including monoclonal antibodies, specific for those peptides, and of using such antibodies in additional tests for detecting lymphocytes capable of binding the peptides.

1. Purification and Characterization of Synthetic SCM-Active Cancer Recognition Peptides Several batches of synthetic experimental allergic encephalitogenic peptide (EAE) produced by Beckman gave a response in the SCM test that was similar to the response given to cancer basic protein (CaBP) or other cancer-associated antigens. That is, lymphocytes isolated from patents with malignant diseases responded to challenge with EAE by a decrease in the value of P in the SCM test, while lymphocytes isolated from healthy donors or with donors with various non-malignant diseases gave no response in the test. The only exception, as expected, was multiple sclerosis.

At a later time, preparations of Beckman EAE were further purified by anion-exchange chromatography. This purer EAE most unexpectedly failed to produce the expected response in the lymphocytes from patents with malignant diseases. This discovery led to the hypothesis that the previously-observed response in the SCM test was due to impurities in the EAE peptide, rather than the EAE peptide itself. Accordingly, several "impurities" were purified from the older preparations of EAE peptide by anion-exchange chromatography on diethylaminoethyl-cellulose (DEAE-cellulose) in ammonium bicarbonate.

Desalted EAE was lyophilized and then reconstituted in 10 nM aqueous ammonium bicarbonate and loaded at no more than 4% of column volume on an 0.8 cm × 26 cm column of microgranular DEAE-cellulose (Whatman DE-52). The column was washed with 10 ml of 10 mM aqueous ammonium bicarbonate and then eluted at room temperature with a linear gradient of aqueous ammonium bicarbonate increasing in concentration at a rate of 0.1% per minute from 10 mM to 1M ammonium bicarbonate. One ml fractions were collected and aliquots assayed for activity in the SCM test.

In this fractionation, the purified EAE peptide eluted at fraction 51, or at about 0.24M ammonium bicarbonate. The two "impurities" giving activity in the SCM test eluted at fractions 42–44, or 0.19M to 0.20M ammonium bicarbonate, and at fractions 57–61, or 0.27 to 0.29M ammonium bicarbonate, respectively. These peptides were designated Peptide I for the peptide eluting at fractions 42–44 or at 0.19M to 0.20M ammonium bicarbonate, and Peptide II for the peptide eluting at fractions 57–61 or at 0.27M to 0.29M ammonium bicarbonate.

The EAE purified from this fractionation displayed no SCM activity when it was used to challenge lymphocytes from donors with malignant disease. By contrast, the "impurities", Peptides I and II, present at the level of tenths of a percent of the main EAE peak, showed SCM activity when used to challenge such lymphocytes. Table 1 shows the responses in the SCM test when the purified EAE (fraction 51) and the two "impurities," (Peptide I at fractions 42–44 and Peptide II at 57–61) were used to challenge lymphocytes from donors with various malignant diseases, as well as lymphocytes from healthy donors. Again, the SCM activity of the "impurity" peptides was nonspecific with respect to the type of cancer from which the lymphocytes used in the assay came, making such peptides desirable as a challenging material.

The amino acid sequence of EAE itself is known to be Phe-Ser-Trp-Gly-Ala-Glu-Gly-Gln-Arg. Amino acid analysis of Peptide I, eluting at 0.19 to 0.20M ammonium bicarbonate, showed it to be the same as that of the purified SCM-inactive EAE, except that serine and glutamic acid were both missing. Since there is only one serine and one glutamic acid in EAE, Peptide I is an heptapeptide with the sequence Phe-Trp-Gly-Ala-Gly-Gln-Arg (I).

Similarly, amino acid analysis of Peptide II, eluting at 0.27 to 0.29M ammonium bicarbonate, showed that it had the same amino acid composition as EAE except that serine was missing. Therefore Peptide II is a octapeptide with the sequence of Phe-Trp-Gly-Ala-Glu-Gly-Gln-Arg (II). This pattern of elution is logical as the glutamate-containing peptide would be expected to be more negatively charged at neutral pH and bind more tightly to the positively charged DEAE-cellulose column.

The amino acid composition of these peptides was determined after hydrolysis of the dried peptides with 2% thioglycolic acid in 6N HCl in sealed glass ampules under nitrogen. After the hydrolysates were lyophilized, the residues were dissolved with 2% sodium dodecyl sulfate (SDS) in 0.04M sodium borate buffer. The amino acids were determined by their fluorescence as o-phthaldialdehyde derivatives after high pressure liquid chromatography (HPLC) as described in "Amino Acid Analysis by HPLC," Beckman, Altex Division, Berkeley, Calif. 94710.

It is believed that a peptide of similar structure lacking glutamic acid but containing serine with the amino acid sequence Phe-Ser-Trp-Gly-Ala-Gly-Gln-Arg (III), designated Peptide III, is similarly active in the SCM test. It is known that a somewhat longer peptide isolated from lymphocytes from donors with cancer and itself having SCM activity has serine; this longer peptide has the approximate amino acid composition ($Asx_2$, $Glx_3$, Ser, His, $Gly_5$, Thr, Arg, $Ala_3$, Tyr, $Met_2$, $Val_3$, $Phe_3$, Ile, $Leu_3$). The presence of serine in this SCM-active peptide leads to the conclusion that the presence of serine in the peptide does not necessarily abolish SCM activity.

Similarly, the fact that a somewhat longer peptide than these 7 or 8 amino acid peptides isolated as impurities from EAE also shows SCM activity suggests that the sequences I, II, or III may be incorporated as part of a larger sequence without eliminating SCM activity. Therefore, such longer sequences containing sequence I, II, or III should also be considered part of the invention.

It is also a well-established principle of protein chemistry that certain amino acid substitutions, entitled "conservative" amino acid substitutions, can be made in a peptide without alternating either the conformation or the function of that peptide. Such changes affecting amino acids in Peptides I, II, or III include Val for Ala, Asp for Glu, Asn for Gln, and Thr for Ser. Accordingly, it is believed that altered peptide molecules having the structure of I, II, or III in which any or all of the above-described conservative amino acid substitutions are made, exhibit SCM activity, and accordingly are considered part of the invention disclosed herein.

2. Use of the Synthetic Peptides in the SCM Test

These synthetic peptides are useful in the SCM test for the detection of malignancies, and a number of examples in which lymphocytes from patients with various forms of cancer were challenged with either Peptide I or Peptide II are shown in Table 1.

To perform the SCM test, the subpopulation of lymphocytes described as "potentially SCM-responding lymphocytes" is separated from the peripheral blood of the person to be tested. This separation can be performed by the methods described in L. Cercek and B. Cercek, "Application of the Phenomenon of Changes in the Structuredness of Cytoplasmic Matrix (SCM) in the Diagnosis of Malignant Disorders: A Review," *Europ. J. Cancer*, 13, 903–915 (1977), and in the prior patent application by the Cerceks entitled "Automated Collection of Buoyant Density Specific Cells from Density Gradients," Ser. No. 838,264, filed Mar. 10, 1986. These methods basically involve removing the phagocytic cells by treating the lymphocytes with iron powder and then centrifuging the lymphocytes through a Ficoll TM -Trisil TM density gradient solution. The lymphocytes characterized as "potentially SCM-responding lymphocytes" have a buoyant density of about 1.059 g/cm$^3$ to about 1.067 g/cm$^3$ at 20° C. and an osmolality of about 0.315 to about 0.320 Osm/kg.

Once the appropriate lymphocytes have been isolated, the SCM test is performed according to the methods described in the *European Journal of Cancer* article and in the prior patent application by the Cerceks entitled "Method for Measuring Polarized Fluorescence Emissions," Ser. No. 867,079, filed May 27, 1986. The SCM test measures the decrease in fluorescence polarization after the lymphocytes have been incubated with a challenging agent, either a cancer-associated antigen such as a synthetic peptide of the present invention, or, alternatively, with a mitogen such as phytohaemagglutinin, concanavalin A, or pokeweed mitogen. As stated, lymphocytes from cancer patients respond with a decrease in the measured fluorescence polarization to cancer-associated antigens, including the synthetic peptides of the present invention, and not to mitogens, while lymphocytes from persons free of malignant diseases respond only to mitogens and not to the cancer-associated antigens.

Since the intrinsic fluorescence of cellular components is very small, an extrinsic fluor must be used. Accordingly, the compound fluorescein diacetate (FDA) is added to the cells. FDA itself is nonfluorogenic, but is taken up by the lymphocytes and hydrolyzed intracellularly by enzymatic action to the fluorescent compound fluorescein.

These measurements of the SCM in living cells are carried out on cell suspensions in a fluorescence spectrophotometer equipped with a polarizer designed to pass vertically polarized light between the excitation monochromator an the cell sample, and with a rotatable analyzer capable of passing either vertically or horizontally polarized light between the cell sample and the emission monochromator. The complete assembly of fluorescence spectrophotometer, polarizer, and analyzer is designated a "fluorescence polarization measuring apparatus."

Although the selection of excitation and emission wavelengths is a matter of choice and the optimal wavelength depends on the fluorogenic agent employed, when FDA is used as the source of the fluorogenic agent best results have been obtained using an excitation wavelength of 470 nm and an emission wavelength of 510 nm. All examples described subsequently herein use that combination of wavelengths using a xenon lamp as the light source. Good results have also been achieved using an excitation wavelength of 442 nm and an emission wavelength of 527 nm.

The fluorescence polarization values obtained must be correct for the fluorescein fluorescence polarization observed in the suspension which is not intracellular in nature, as only the intracellular response is properly measured in the SCM test. When this test is performed, the polarization, P, or the emitted light from an aliquot of the lymphocytes stimulated with a cancer-associated antigen, such as a composition or synthetic peptide of the present invention, or, alternatively, with a mitogen, is compared with the polarization of the emitted light from an aliquot of control lymphocytes that have not been stimulated with either a cancer-associated antigen or a mitogen.

To express the response of the lymphocytes to the cancer-associated antigen and to increase the resolution of the SCM test the SCM response ratio, $RR_{SCM}$, is calculated. The $RR_{SCM}$ value is the ratio of the degree of fluorescence polarization obtained after stimulation with the cancer-associated antigen, $P_{CAA}$, over that after PHA stimulation, $P_{PHA}$, both measured at comparable times after 30–100 min of incubation:

$$RR_{SCM} = P_{CAA}/P_{PHA}$$

When the SCM test is performed with a synthetic peptide of the present invention, the response obtained is independent of the type of malignancy affecting the donor of the lymphocytes. Lymphocytes from patients with many diverse forms of cancer give a similar response when such synthetic peptides are used to challenge them in the SCM test (Table 1). Lymphocytes from donors with cancer of the cervix, mouth, and larynx all gave positive SCM response, shown by a decrease in measured P value, when challenged with Peptide I. Lymphocyte from donors with cancer of the cervix, larynx, and maxillary antrum, as well as from donors with lung oat cell carcinoma and retromolar cancer, all gave a similar positive response when challenged with Peptide II. By contrast, purified EAE itself gave no response when used to challenge lymphocytes from donors with several of these types of malignancies.

3. Preparation and Use of Genetic Probes

Since the amino acid sequences of the synthetic SCM-active cancer recognition peptides are known, it is possible to construct genetic probes consisting of DNA oligonucleotide sequences corresponding to those amino acid sequences. A simple way of doing this is to use the codons corresponding to the four-amino acid sequence seemingly common to all of the SCM-active cancer recognition peptides, Phe-Trp-Gly-Ala. Using all of the possible codon sequences according to the genetic code give a mixture of eight 11-base probes with the following structure:

T—T—[T/C]—T—G—G—G—G—[T/C/A/G]—G—C.

In this structure, the bases in brackets represent alternate bases at that particular position. The last base of the codon for Ala can be any of the four bases, so that base adds nothing to specificity and can be ignored. The necessity of multiple probe sequences exits because the genetic code is degenerate, so that there are two possible codons for Phe, differing in the third position, and four for Gly. Fortunately, there is only one codon for Trp, so that amino acid is a desirable one to have in the sequence. By the use of current oligonucleotide synthesis techniques, it is possible to sequence mixtures of defined sequences of much greater complexity; mixtures of up to 384 separate sequences have been prepared. The preparation and use of mixed probes of this type have been described in R. B. Wallace, M. J. Johnson, T. Hirose, T. Miyake, E. H. Kawashima, and K. Itakura, "The Use of Synthetic Oligonucleotides as Hybridization Probes. II. Hybridization of Oligonucleotides of Mixed Sequence to Rabbit $\beta$-Globin DNA," *Nucl. Acids Res.* 9, 879–894 (1981).

Although this approach to the preparation of genetic probes is most likely the simplest and fastest, it has several drawbacks. The hybridization of such relatively short probes can be nonspecific, and even specific hybridization occurs at a greater frequency within the genome than could be expected. The use of short probes, therefore, can give an unacceptable frequency of false positive hybridization results.

An alternative method is the synthesis and use of single longer probes based on the entire 7- or 8-amino acid sequence of the synthetic SCM-active cancer recognition peptides. These probes are constructed according to the expected frequency of codon utilization in human genes, according to R. Lathe, "Synthetic Oligonucleotide Probes Deduced from Amino Acid Sequence Data: Theoretical and Practical Considerations," *J. Mol. Biol.* 813, 1 (1985). Table 2 presents the optimum probe sequences determined according to Lathe for each of the amino acid sequences expected to have SCM activity, a total of 20 sequences. The advantage of these longer probes is greater specificity, so that the frequency of cross-reactions is markedly lessened when compared with shorter probes. Moreover, exact homology is not needed for accurate hybridization when working with such probes; a few mismatches in a long probe are not fatal.

These genetic probes should be useful for the detection of genes in lymphocytes or other cells which code for sequences homologous to the sequence of the synthetic peptides, and therefore possibly indicative of cancer. Such detection can be accomplished by screening either random genomic clones obtained by a "shotgun" experiment by hybridization, or by screening cDNA prepared by standard methods from mRNA. This latter method offers the advantage of being able to determine when and under what conditions genes coding for sequences homologous to the synthetic peptides are expressed.

4. Antibody Formation and Utilization

The peptide molecules described above as possessing SCM activity are too small to be effectively immunogenic. However, such molecules can produce antibodies when covalently coupled to a high molecular weight protein carrier. The carrier is preferably keyhole limpet hemocyanin, as described in W. J. Gullick, J. Downward, and M. D. Waterfield, "Antibodies the Autophosphorylation Sites of the Epidermal Growth Factor Receptor as Probes of Structure and Function," *EMBO J.* 4, 2869–2877 (1985) and M. B. Rittenberg and A. A. Amkraut, "Immunogenicity of Trinitrophenyl-Hemocyanin: Production of Primary and Secondary Anti-Hapten Precipitins," *J. Immunol.* 97, 421–430 (1966). The carrier can also be a serum albumin such as bovine serum albumin, as described in B. F. Erlanger, "The preparation of Antigenic Hapten-Carrier Conjugates: A Survey," *Methods in Enzymol.* 70, 85–105 (1980). Molecules smaller than the serum albumins, which have molecular weights of approximately 60,000, are not effective carriers, so that the terminology "high molecular weight carrier" means, in this context, protein molecules of at least 60,000 molecular weight. The coupling agent is preferably a carbodiimide, such as the water-soluble carbodiimides 1-ethyl-3-(3-dimethylaminopropyl)carbodiimide and 1-cyclohexyl-3-[2-morpholino-(4)-ethyl]carbodiimide, as described in S. Bauminger and M. Wilchek, "The Use of Carbodiimides in the Preparation of Immunizing Conjugates," *Methods in Enzymol,* 70, 151–159 (1980). The coupling agent can also be glutaraldehyde, as described in M. Reichlin, "Use of Glutaraldehyde as a Coupling agent for Proteins and Peptides," *Methods in Enzymol,* 70, 159–166 (1980), and in the *EMBO J.* article by Gullick, Downward and Waterfield. The covalently coupled conjugate is then used to immunize animals, such as rabbits. Once produced, such antibodies which react specifically with the SCM-active cancer recognition peptide are purified by affinity chromatography.

As a model system for the production of such antibodies, antibodies were produced to the unpurified Beckman EAE, containing Peptides I and II, by coupling the EAE to keyhole limpet hemocyanin with a carbodiimide. This coupling procedure did not inactivate the SCM activities of Peptides I and II.

Antibody-producing cells from the spleens of animals immunized according to the above methods are then isolated and fused with myeloma cells by well-established methods, as described originally in G. Kohler and C. Milstein, "Continuous Cultures of Fused Cells Secreting Antibody of Predefined Specificity," *Nature* 256, 495–497 (1975). The product of such fusion is immortal antibody-producing myeloma cells. This method encompasses cell fusion of the antibody-producing spleen cells with HGPRT myeloma cells using polyethylene glycol, followed by the selection of the fused cells produced thereby in the presence of hypoxanthine, thymidine, and aminopterin, and then screening the hybridoma cells for the antibody of interest. The hybridoma cells produced thereby secrete their antibodies into the culture medium, providing a source of monoclonal antibodies specific against one antigenic determinant or epitope.

Once isolated, such antibodies can be used in a number of immunological assays which can provide an alternative method of screening for malignancies. For example, the antibodies can be used in an immunochemical assay for screening lymphocytes by purifying the potentially SCM-responding subpopulation of lymphocytes by density gradient centrifugation, incubating the lymphocytes with the SCM-active cancer recognition peptide to form a lymphocyte-peptide complex, and then reacting the complex with an antibody specific for the peptide. Such antibodies can then be detected either by having a fluorescent or radioactive label coupled directly to the antibodies, or by using a second antibody specific for the first antibody and covalently linked to an enzyme and assaying for the enzymatic activity in the frequently used enzyme-linked immunosorbent (ELISA) test.

Such immunochemical assays can provide a sensitive technique for spotting lymphocytes that can bind and react with SCM-active peptides. Since normal lymphocytes do not respond to the SCM-active peptides, while responses to the peptides can be triggered within 1 hour after the implantation of $3.5 \times 10^5$ Ehrlich ascites cells into mice (equivalent on the basis of body weight to less than $10^9$ tumor cells in humans), this test can be useful in spotting the first signs of malignancy, and can give a positive result long before overt clinical or histological signs of cancer are detectable.

Although the present invention has been described in considerable detail with regard to certain preferred versions thereof, other versions are possible. Therefore the spirit and scope of the appended claims should not be limited to the description of the preferred versions container herein.

TABLE 1

SCM-RESPONSES (AS % OF CONTROL) TO FRACTIONS OF BECKMAN EAE

| DIAGNOSIS OF BLOOD DONOR | SCM-ACTIVE COMPOSITION: | | | |
|---|---|---|---|---|
| | BECKMAN EAE | PURIFIED EAE | PEPTIDE I | PEPTIDE II |
| Ca-mouth | 84.9, 86.0 | 100.0 | 86.0 | — |
| Ca-maxillary antrum | 81.8 | 100.5 | — | 76.0 |
| Ca-larynx | 84.3, 87.0 85.0 | 100.0 | 84.2 | 79.0, 83.0 |
| Ca-cervix uteri | 84.4, 86.0 87.0 | 99.5 | 82.0 | 79.0 |
| Lung oat cell carcinoma | 82.0 | — | — | 80.6 |
| Ca-retromolar | — | — | — | 81.0 |
| Healthy donors (2) | — | 100.5 | — | — |

Ca = cancer
"Beckman EAE" is the EAE originally distributed by Beckman Instruments and used in the SCM assay without further purification.
"Purified EAE" is the EAE purified away from contaminants and eluting at fraction 51 from the DEAE-cellulose column.
"Peptide I" is one of the peptides purified from Beckman EAE and eluting at fractions 42-44.
"Peptide II" is the other peptide purified from Beckman EAE and eluting at fraction 57.

TABLE 2

SEQUENCE OF DNA PROBES CORRESPONDING TO SCM-ACTIVE PEPTIDES

Peptide I and Variants Produced by Conservative Amino Acid Substitutions:

Phe—Trp—Gly—Ala—Gly—Gln—Arg (I)
TTC—TGG—GGC—GCT—GGC—CAG—CGG

Phe—Trp—Gly—Val—Gly—Gln—Arg (Ia)
TTC—TGG—GGC—GTG—GGC—CAG—CGG

Phe—Trp—Gly—Ala—Gly—Asn—Arg (Ib)
TTC—TGG—GGC—GCT—GGC—AAC—CGG

Phe—Trp—Gly—Val—Gly—Asn—Arg (Ic)
TTC—TGG—GGC—GTG—GGC—AAC—CGG

Peptide II and Variants Produced by Conservative Amino Acid Substitutions:

Phe—Trp—Gly—Ala—Glu—Gly—Gln—Arg (II)
TTC—TGG—GGC—GCT—GAG—GGC—CAG—CGG

Phe—Trp—Gly—Val—Glu—Gly—Gln—Arg (IIa)
TTC—TGG—GGC—GTG—GAG—GGC—CAG—CGG

TABLE 2-continued

SEQUENCE OF DNA PROBES CORRESPONDING TO SCM-ACTIVE PEPTIDES

Phe—Trp—Gly—Ala—Asp—Gly—Gln—Arg (IIb)
TTC—TGG—GGC—GCT—GAT—GGC—CAG—CGG

Phe—Trp—Gly—Ala—Glu—Gly—Asn—Arg (IIc)
TTC—TGG—GGC—GCT—GAG—GGC—AAC—CGG

Phe—Trp—Gly—Val—Asp—Gly—Gln—Arg (IId)
TTC—TGG—GGC—GTG—GAT—GGC—CAG—CGG

Phe—Trp—Gly—Val—Glu—Gly—Asn—Arg (IIe)
TTC—TGG—GGC—GTC—GAG—GGC—AAC—CGG

Phe—Trp—Gly—Ala—Asp—Gly—Asn—Arg (IIf)
TTC—TGG—GGC—GCT—GAT—GGC—AAC—CGG

Phe—Trp—Gly—Val—Asp—Gly—Asn—Arg (IIg)
TTC—TGG—GGC—GTG—GAT—GGC—AAC—CGG

Peptide III and Variants Produced by Conservative Amino Acid Substitutions

Phe—Ser—Trp—Gly—Ala—Gly—Gln—Arg (III)
TTC—TCC—TGG—GGC—GCT—GGC—CAG—CGG

Phe—Thr—Trp—Gly—Ala—Gly—Gln—Arg (IIIa)
TTC—ACC—TGG—GGC—GCT—GGC—CAG—CGG

Phe—Ser—Trp—Gly—Val—Gly—Gln—Arg (IIIb)
TTC—TCC—TGG—GGC—GTC—GGC—CAG—CGG

Phe—Ser—Trp—Gly—Ala—Gly—Asn—Arg (IIIc)
TTC—TCC—TGG—GGC—GCT—GGC—AAC—CGG

Phe—Thr—Trp—Gly—Val—Gly—Gln—Arg (IIId)
TTC—ACC—TGG—GGC—GTG—GGC—CAG—CGG

Phe—Thr—Trp—Gly—Ala—Gly—Asn—Arg (IIIe)
TTC—ACC—TGG—GGC—GCT—GGC—AAC—CGG

Phe—Ser—Trp—Gly—Val—Gly—Asn—Arg (IIIf)
TTC—TCC—TGG—GGC—GTG—GGC—AAC—CGG

TABLE 2-continued

SEQUENCE OF DNA PROBES CORRESPONDING
TO SCM-ACTIVE PEPTIDES

Phe—Thr—Trp—Gly—Val—Gly—Asn—Arg (IIIg)
TTC—ACC—TGG—GGC—GTG—GGC—AAC—CGG

Amino acids altered by substitution from the peptides I, II, or III are underlined. The codon assignments are taken from R. Lathe, "Synthetic Oligonucleotide Probes Deduced from Amino Acid Sequence Data: Theoretical and Practical Considerations," J. Mol. Biol. 183, 1-12 (1985), and are designed to be optimal for the normal codon utilization in human DNA as determined by a study of a large number of human coding sequences.

What is claimed is:

1. A composition comprising a peptide of the amino acid sequence F-W-G-A-E-G-Q-R, the composition being active in the structuredness of the cytoplasmic matrix (SCM) test and being substantially free of experimental allergic encephalitogenic peptide.

2. A composition comprising a peptide of the amino acid sequence F-W-G-A-G-Q-R, the composition being active in the structuredness of the cytoplasmic matrix (SCM) test and being substantially free of experimental allergic encephalitogenic peptide.

3. A method for testing T-cell mononuclear lymphocytes obtained from a mammalian donor for the presence or absence of malignancy detectable by the structuredness of the cytoplasmic matrix (SCM) test, the method comprising the steps of:
   (a) extracellularly contacting a suspension of the lymphocytes with a composition active in the SCM test, the composition comprising a peptide of the amino acid sequence F-W-G-A-E-G-N-R substantially free of experimental allergic encephalitogenic peptide, the quantity of the composition being sufficient to reduce the structuredness of the cytoplasmic matrix of lymphocytes from a donor having a malignancy and insufficient to reduce the structuredness of the cytoplasmic matrix of lymphocytes from a donor free of malignancy; and
   (b) determining the structuredness of the cytoplasmic matrix of lymphocytes contacted with the SCM-active composition in step (a) by fluorescence polarization in order to determine the presence or absence of malignancy in the donor of the lymphocytes.

4. The method of claim 3 wherein the step of determining the decrease in the structuredness of the cytoplasmic matrix comprises the steps of:
   (a) providing a first aliquot of the suspension of the lymphocytes, the first aliquot having been contacted with the SCM-active cancer recognition peptide;
   (b) providing a second aliquot of the suspension of the lymphocytes, the second aliquot not having been contacted with the SCM-active cancer recognition peptide;
   (c) contacting both the first and second aliquots individually with the same extrinsic fluorophore in such manner that the extrinsic fluorophore is taken up by the lymphocytes;
   (d) measuring the fluorescence polarization, $P_S$, from the first aliquot contacted with the extrinsic fluorophore;
   (e) measuring the fluorescence polarization, $P_C$, from the second aliquot contacted with the fluorophore; and
   (f) determining the ratio of $P_S$ to $P_C$, whereby a ratio of $P_S$ to $P_C$ of less than about 0.9 indicates the presence of malignancy in the donor of the lymphocytes.

5. The method of claim 3 wherein the step of determining the decrease in the structuredness of the cytoplasmic matrix comprises the steps of:
   (a) providing a first aliquot of the suspension of the lymphocytes, the first aliquot having been contacted with the SCM-active cancer recognition peptide;
   (b) providing a second aliquot of the suspension of the lymphocytes, the second aliquot having been contacted with a mitogen selected from the group consisting of phytohaemagglutinin, concanavalin A, and pokeweed mitogen;
   (c) contacting both the first and second aliquots individually with the same extrinsic fluorophore in such manner that the extrinsic fluorophore is taken up by the lymphocytes;
   (d) measuring the fluorescence polarization, $P_S$, from the first aliquot contacted with the extrinsic fluorophore;
   (e) measuring the fluorescence polarization, $P_M$, from the second aliquot contacted with the extrinsic fluorophore; and
   (f) determining an SCM response ratio, $RR_{SCM}$, as the ratio of $P_S$ to $P_M$, whereby an $RR_{SCM}$ of less than about 0.8 indicates the presence of malignancy in the donor of the lymphocytes.

6. A method for testing T-cell mononuclear lymphocytes obtained from a mammalian donor for the presence or absence of malignancy detectable by the structuredness of the cytoplasmic matrix (SCM) test, the method comprising the steps of:
   (a) extracellularly contacting a suspension of the lymphocytes with a composition active in the SCM test, the composition comprising a peptide of the amino acid sequence F-W-G-A-G-Q-R substantially free of experimental allergic encephalitogenic peptide, the quantity of the composition being sufficient to reduce the structuredness of the cytoplasmic matrix of the lymphocytes from a donor having a malignancy and insufficient to reduce the structuredness of the cytoplasmic matrix of lymphocytes from a donor free from malignancy; and
   (b) determining the structuredness of the cytoplasmic matrix of the lymphocytes contacted with the SCM-active composition in step (a) by fluorescence polarization in order to determine the presence or absence of malignancy in the donor of the lymphocytes.

7. The method of claim 6 wherein the step of determining the decrease in the structuredness of the cytoplasmic matrix comprises the steps of:
   (a) providing a first aliquot of the suspension of the lymphocytes, the first aliquot having been contacted with the SCM-active cancer recognition peptide;
   (b) providing a second aliquot of the suspension of the lymphocytes, the second aliquot not having been contacted with the SCM-active cancer recognition peptide;
   (c) contacting both the first and second aliquots individually with the same extrinsic fluorophore in such manner that the extrinsic fluorophore is taken up by the lymphocytes;

(d) measuring the fluorescence polarization, $P_S$, from the first aliquot contacted with the extrinsic fluorophore;

(e) measuring the fluorescence polarization, $P_C$, from the second aliquot contacted with the fluorophore; and (f) determining the ratio of $P_S$ to $P_C$, whereby a ratio of $P_S$ to $P_C$ of less than about 0.9 indicates the presence of malignancy in the donor of the lymphocytes.

8. The method of claim 6 wherein the step of determining the decrease in the structuredness of the cytoplasmic matrix comprises the steps of:

(a) providing a first aliquot of the suspension of the lymphocytes, the first aliquot having been contacted with the SCM-active cancer recognition peptide;

(b) providing a second aliquot of the suspension of the lymphocytes, the second aliquot having been contacted with a mitogen selected from the group consisting of phytohaemagglutinin, concanavalin A, and pokeweed mitogen;

(c) contacting both the first and second aliquots individually with the same extrinsic fluorophore in such manner that the extrinsic fluorophore is taken up by the lymphocytes;

(d) measuring the fluorescence polarization, $P_S$, from the first aliquot contacted with the extrinsic fluorophore;

(e) measuring the fluorescence polarization, $P_M$, from the second aliquot contacted with the extrinsic fluorophore; and (f) determining an SCM response ratio, $RR_{SCM}$, as the ratio of $P_S$ to $P_M$, whereby an $RR_{SCM}$ of less than about 0.8 indicates the presence of malignancy in the donor of the lymphocytes.

9. A composition comprising a peptide selected from the group consisting of F-W-G-$X_1$-G-$X_3$-R, wherein $X_1$ is selected from the group consisting of A and V, and $X_3$ is selected from the group consisting of O and N, the composition being active in the structuredness of the cytoplasmic matrix (SCM) test and being substantially free of experimental allergic encephalitogenic peptide.

10. A method for testing T-cell mononuclear lymphocytes obtained from a mammalian donor for the presence or absence of malignancy detectable by the structuredness of the cytoplasmic matrix (SCM) test, the method comprising the steps of:

(a) extracellularly contacting a suspension of the lymphocytes with a composition active in the SCM test, the composition comprising a peptide selected from the group consisting of F-W-G-$X_1$-G-$X_3$-R, wherein $X_1$ is selected from the group consisting of A and V, and $X_3$ is selected from the group consisting of O and N, the composition being substantially free of experimental allergic encephalitogenic peptide, the quantity of the SCM-active composition being sufficient to reduce the structuredness of the cytoplasmic matrix of lymphocytes from a donor having a malignancy and insufficient to reduce the structuredness of the cytoplasmic matrix of lymphocytes from a donor free from malignancy; and (b) determining the structuredness of the cytoplasmic matrix of the lymphocytes contacted in step (a) by fluorescence polarization in order to determine the presence or absence of malignancy in the donor of the lymphocytes.

11. The method of claim 10 wherein the step of determining the decrease in the structuredness of the cytoplasmic matrix comprises the steps of:

(a) providing a first aliquot of the suspension of the lymphocytes, the first aliquot having been contacted with the SCM-active composition;

(b) providing a second aliquot of the suspension of the lymphocytes, the second aliquot not having been contacted with the SCM-active composition;

(c) contacting both the first and second aliquots individually with the same extrinsic fluorophore in such manner that the extrinsic fluorophore is taken up by the lymphocytes;

(d) measuring the fluorescence polarization, $P_S$, from the first aliquot contacted with the extrinsic fluorophore;

(e) measuring the fluorescence polarization, $P_C$, from the second aliquot contacted with the fluorophore; and (f) determining the ratio of $P_S$ to $P_C$, whereby a ratio of $P_S$ to $P_C$ of less than about 0.9 indicates the presence of malignancy in the donor of the lymphocytes.

12. The method of claim 10 wherein the step of determining the decrease in the structuredness of the cytoplasmic matrix comprises the steps of:

(a) providing a first aliquot of the suspension of the lymphocytes, the first aliquot having been contacted with the SCM-active composition;

(b) providing a second aliquot of the suspension of the lymphocytes, the second aliquot having been contacted with a mitogen selected from the group consisting of phytohaemagglutinin, concanavalin A, and pokeweed mitogen;

(c) contacting both the first and second aliquots individually with the same extrinsic fluorophore in such manner that the extrinsic fluorophore is taken up by the lymphocytes;

(d) measuring the fluorescence polarization, $P_S$, from the first aliquot contacted with the extrinsic fluorophore;

(e) measuring the fluorescence polarization, $P_M$, from the second aliquot contacted with the extrinsic fluorophore; and (f) determining an SCM response ratio, $RR_{SCM}$, as the ratio of $P_S$ to $P_M$, whereby an $RR_{SCM}$ of less than about 0.8 indicates the presence of malignancy in the donor of the lymphocytes.

13. A composition comprising a peptide selected from the group consisting of F-W-G-$X_1$-$X_2$-G-$X_3$-R, wherein $X_1$ is selected from the group consisting of A and V, $X_2$ is selected from the group consisting of E and D, and $X_3$ is selected from the group consisting of O and N, the composition being active in the structuredness of the cytoplasmic matrix test and being substantially free of experimental allergic encephalitogenic peptide.

14. A method for testing T-cell mononuclear lymphocytes obtained from a mammalian donor for the presence or absence of malignancy detectable by the structuredness of the cytoplasmic matrix (SCM) test, the method comprising the steps of:

(a) extracellularly contacting a suspension of the lymphocytes with a composition active in the SCM test, the composition comprising a peptide selected from the group consisting of F-W-G-$X_1$-$X_2$-G-$X_3$-R, wherein $X_1$ is selected from the group consisting of A and V, $X_2$ is selected from the group consisting of E and D, and $X_3$ is selected from the group consisting of O and N, the composition being substantially free of experimental allergic encephalitogenic peptide, the quantity of the SCM-active composition being sufficient to reduce the structuredness of the cytoplasmic matrix of lymphocytes from a donor having a malignancy and insufficient to reduce the structuredness of the cytoplasmic matrix of lymphocytes from a donor free of malignancy; and (b) determining the structuredness of the cytoplasmic matrix of the lymphocytes contacted in step (a) by fluorescence polarization in order to determine the presence or absence of malignancy in the donor of the lymphocytes.

15. The method of claim 14 wherein the step of determining the decrease in the structuredness of the cytoplasmic matrix comprises the steps of:
  (a) providing a first aliquot of the suspension of the lymphocytes, the first aliquot having been contacted with the SCM-active composition;
  (b) providing a second aliquot of the suspension of the lymphocytes, the second aliquot not having been contacted with the SCM-active composition;
  (c) contacting both the first and second aliquots individually with the same extrinsic fluorophore in such manner that the extrinsic fluorophore is taken up by the lymphocytes;
  (d) measuring the fluorescence polarization, $P_S$, from the first aliquot contacted with the extrinsic fluorophore;
  (e) measuring the fluorescence polarization, $P_C$, from the second aliquot contacted with the fluorophore; and
  (f) determining the ratio of $P_S$ to $P_C$, whereby a ratio of $P_S$ to $P_C$ of less than about 0.9 indicates the presence of malignancy in the donor of the lymphocytes.

16. The method of claim 14 wherein the step of determining the decrease in the structuredness of the cytoplasmic matrix comprises the steps of:
  (a) providing a first aliquot of the suspension of the lymphocytes, the first aliquot having been contacted with the SCM-active composition;
  (b) providing a second aliquot of the suspension of the lymphocytes, the second aliquot having been contacted with a mitogen selected from the group consisting of phytohaemagglutinin, concanavalin A, and pokeweed mitogen;
  (c) contacting both the first and second aliquots individually with the same extrinsic fluorophore in such manner that the extrinsic fluorophore is taken up by the lymphocytes;
  (d) measuring the fluorescence polarization, $P_S$, from the first aliquot contacted with the extrinsic fluorophore;
  (e) measuring the fluorescence polarization, $P_M$, from the second aliquot contacted with the extrinsic fluorophore; and
  (f) determining an SCM response ratio, $RR_{SCM}$, as the ratio of $P_S$ to $P_M$, whereby an $RR_{SCM}$ of less than about 0.8 indicates the presence of malignancy in the donor of the lymphocytes.

17. A composition comprising a peptide having seven or eight amino acid residues, including a sequence selected from the group consisting of F-W-G-$X_1$-$X_2$, where $X_1$ is selected from the group consisting of A and V, and $X_2$ is selected from the group consisting of E and D, the composition being active in the structuredness of the cytoplasmic matrix (SCM) test and being substantially free of experimental allergic encephalitogenic peptide.

18. A method for testing T-cell mononuclear lymphocytes obtained from a mammalian donor for the presence or absence of malignancy detectable by the structuredness of the cytoplasmic matrix (SCM) test, the method comprising the steps of:
  (a) extracellularly contacting a suspension of the lymphocytes with a composition active in the SCM test, the composition comprising a peptide having seven or eight amino acid residues, including a sequence selected from the group consisting of F-W-G-$X_1$-$X_2$, where $X_1$ is selected from the group consisting of A and V, and $X_2$ is selected from the group consisting of E and D, the composition being substantially free of experimental allergic encephalitogenic peptide, the quantity of the SCM-active composition being sufficient to reduce the structuredness of the cytoplasmic matrix of lymphocytes from a donor having a malignancy and insufficient to reduce the structuredness of the cytoplasmic matrix of lymphocytes from a donor free from malignancy; and
  (b) determining the structuredness of the cytoplasmic matrix of the lymphocytes contacted in (a) by fluorescence polarization in order to determine the presence or absence of malignancy in the donor of the lymphocytes.

19. The method of claim 18 wherein the step of determining the decrease in the structuredness of the cytoplasmic matrix comprises the steps of:
  (a) providing a first aliquot of the suspension of the lymphocytes, the first aliquot having been contacted with the SCM-active composition;
  (b) providing a second aliquot of the suspension of the lymphocytes, the second aliquot not having been contacted with the SCM-active composition;
  (c) contacting both the first and second aliquots individually with the same extrinsic fluorophore in such manner that the extrinsic fluorophore is taken up by the lymphocytes;
  (d) measuring the fluorescence polarization, $P_S$, from the first aliquot contacted with the extrinsic fluorophore;
  (e) measuring the fluorescence polarization, $P_C$, from the second aliquot contacted with the fluorophore; and
  (f) determining the ratio of $P_S$ to $P_C$, whereby a ratio of $P_S$ to $P_C$ of less than about 0.9 indicates the presence of malignancy in the donor of the lymphocytes.

20. The method of claim 18 wherein the step of determining the decrease in the structuredness of the cytoplasmic matrix comprises the steps of:
  (a) providing a first aliquot of the suspension of the lymphocytes, the first aliquot having been contacted with the SCM-active composition;
  (b) providing a second aliquot of the suspension of the lymphocytes, the second aliquot having been contacted with a mitogen selected from the group consisting of phytohaemagglutinin, concanavalin A, and pokeweed mitogen;
  (c) contacting both the first and second aliquots individually with the same extrinsic fluorophore in such manner that the extrinsic fluorophore is taken up by the lymphocytes;

(d) measuring the fluorescence polarization, $P_S$, from the first aliquot contacted with the extrinsic fluorophore;

(e) measuring the fluorescence polarization, $P_M$, from the second aliquot contacted with the extrinsic fluorophore; and (f) determining an SCM response ratio, $PR_{SCM}$, as the ratio of $P_S$ to $P_M$, whereby an $RR_{SCM}$ of less than about 0.8 indicates the presence of malignancy in the donor of the lymphocytes.

* * * * *